United States Patent [19]

Margules

[11] 4,432,366
[45] Feb. 21, 1984

[54] REFERENCE ELECTRODE CATHETER

[75] Inventor: Gary S. Margules, Miami, Fla.

[73] Assignee: Cordis Corporation, Miami, Fla.

[21] Appl. No.: 325,402

[22] Filed: Nov. 27, 1981

[51] Int. Cl.³ .............................................. A61B 5/00
[52] U.S. Cl. ..................................... 128/635; 204/403;
204/414; 204/415; 204/435
[58] Field of Search .................... 128/635; 204/195 B,
204/195 P, 403, 414, 415, 435, 433

[56] References Cited

U.S. PATENT DOCUMENTS

| | | | |
|---|---|---|---|
| 3,682,159 | 8/1972 | Imredy et al. | 128/635 |
| 3,912,614 | 10/1975 | Spracklen et al. | 204/195 B |
| 3,979,274 | 9/1976 | Newman | 204/195 B |
| 4,041,933 | 8/1977 | Reichenberger | 128/635 |
| 4,120,292 | 10/1978 | LeBlanc, Jr. et al. | 128/635 |
| 4,176,659 | 12/1979 | Rolfe | 128/635 |
| 4,177,126 | 12/1979 | Imaki | 204/195 R |
| 4,199,412 | 4/1980 | Battaglia et al. | 204/1 T |
| 4,235,687 | 11/1980 | Romette | 204/195 M |
| 4,250,010 | 2/1981 | Kondo et al. | 204/195 M |
| 4,265,250 | 5/1981 | Parker | 125/635 |
| 4,273,636 | 6/1981 | Shimada | 204/195 P |

FOREIGN PATENT DOCUMENTS 15075 9/1980 European Pat. Off. ............ 125/635

Primary Examiner—Lee S. Cohen
Attorney, Agent, or Firm—Henry W. Collins; Thomas R. Vigil

[57] ABSTRACT

A reference electrode catheter for use for in vivo measurement of body fluids. The catheter includes a small diameter cylindrical tube having a reference electrode assembly disposed on the distal end thereof. The reference electrode assembly includes a hollow cylindrical housing and an electrode element positioned within the housing mounted on and supported by a retainer member. The electrode element is connected to an electrical conductor which extends out of the housing and through the passageway of the tubing to the proximal end of the tubing. An electrolytic material, such as gelled Ringer's solution, is disposed within the housing, and a membrane formed of hydrogel is positioned across an aperture in the housing so as to form an ion diffusion barrier between the body fluids to be measured and the electrolytic material within the housing.

18 Claims, 4 Drawing Figures

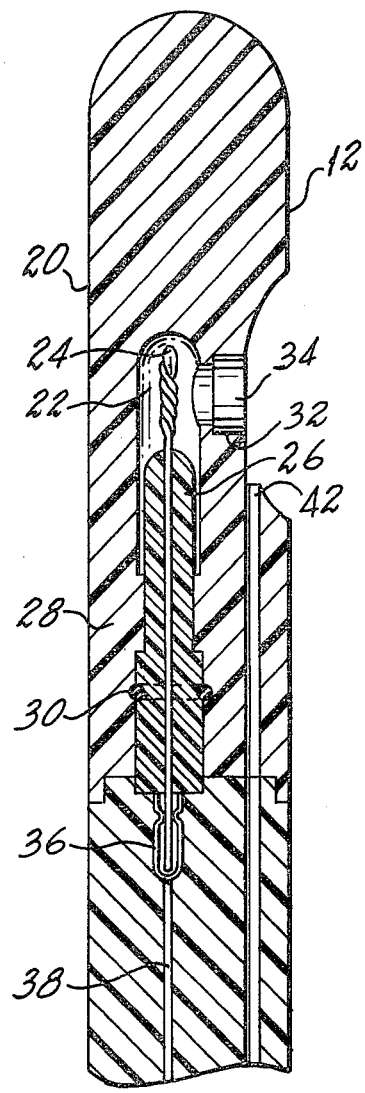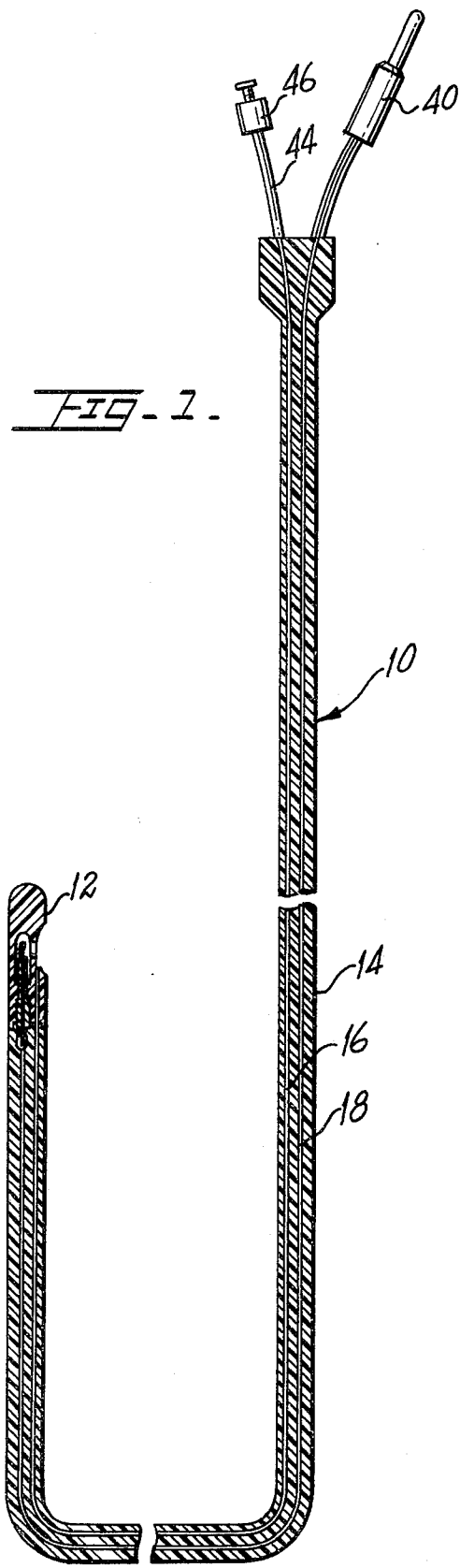

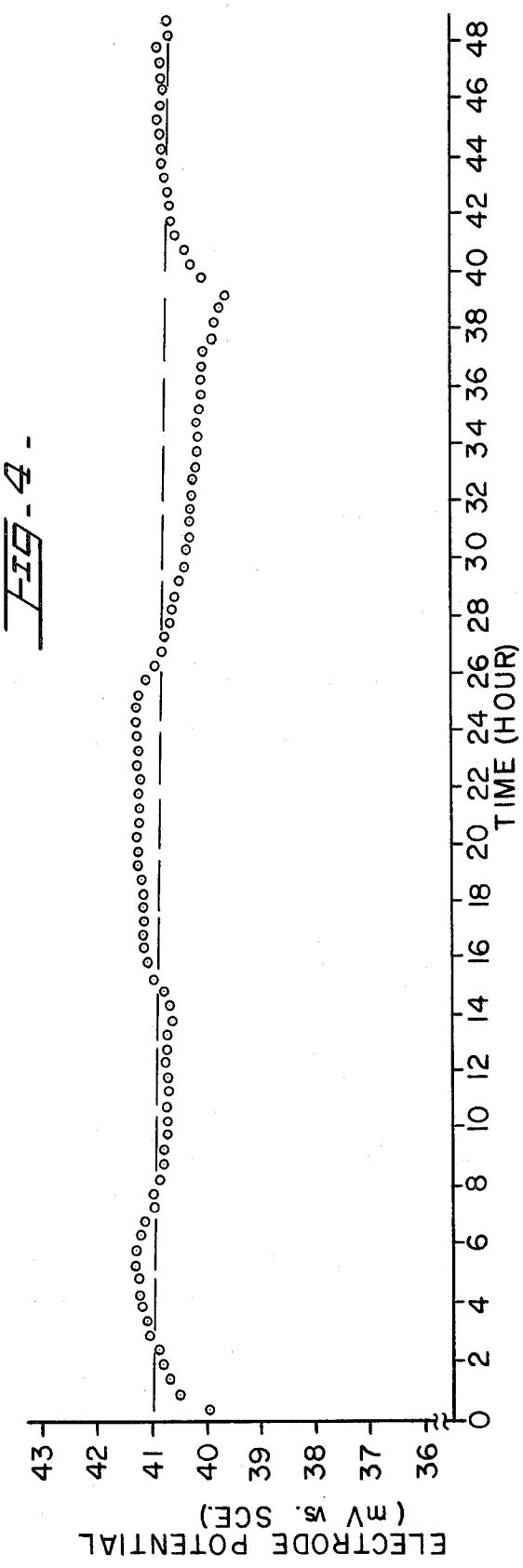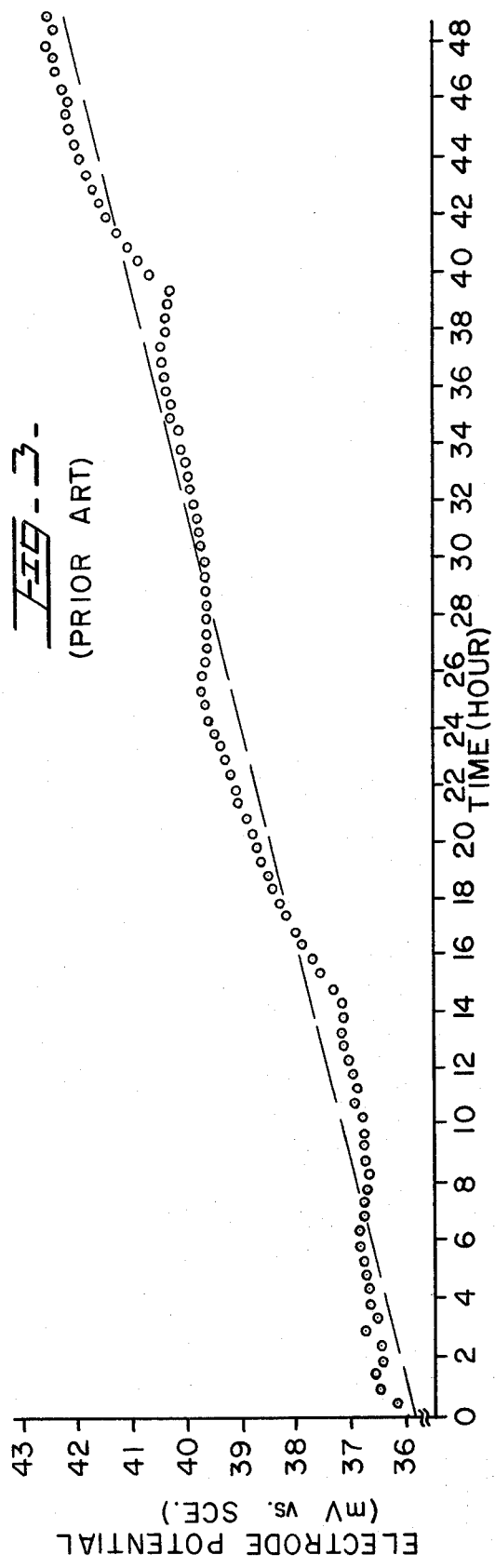

REFERENCE ELECTRODE CATHETER

BACKGROUND OF THE INVENTION

The present invention relates to a reference electrode which may be used to measure a reference potential in various body fluids, such as blood, serum, cerebrospinal fluid or lymph. More particularly, the present invention relates to a reference electrode catheter which may be used in vivo for measuring such body fluids.

Reference electrodes for measuring various bodily fluids are well known. These electrodes generally include an outer housing member, an electrode positioned within the housing member, a liquid electrolyte disposed within the housing, and a porous liquid junction formed in one of the walls of the housing to provide an interface between the body fluid to be measured and the liquid electrolyte within the housing.

The porous liquid junctions have generally been formed of a porous ceramic material. One of the problems inherent in the use of porous ceramic junctions is the fact that certain body fluids tend to coagulate on the surface of the ceramic material and the pores in the ceramic material are very quickly blocked by various solid materials, such as proteins when the electrode is used for the measurement of blood or serum.

Another type of material has been proposed for the porous liquid junction. This material, takes the form of a hydrophilic polypropylene which is coated with a surface active agent. An example of a reference electrode which utilizes such a material for the liquid junction is disclosed in U.S. Pat. No. 4,177,126. Liquid junctions of polypropylene construction provide a satisfactory interface between the body fluids and the electrolyte within the reference electrode, for a limited period of time, however certain body fluids, such as blood, tend to coagulate on the surface of this material with a resultant change in the liquid junction potential after a period of time.

The sole function of a reference electrode is that of providing a very precise measurement of the reference potential of a fluid. Accordingly, any change or drift in the reference electrode results in corresponding inaccuracies in the total measurement taken of the fluid. As the pores in the liquid junction become clogged with organic substances, such as protein substances, the ion diffusion through the liquid junction is altered along with the associated liquid junction potential to thereby cause the electric signal developed by the reference electrode to change or drift. Even a slight drift in the signal, or slight instability in the reference electrode, results in inaccuracies in the total measurements taken of the body fluid.

When a reference electrode is utilized with a catheter for providing in vivo measurement of body fluids, it is imperative that the reference electrode exhibit the characteristic of having long term stability. It is particularly important that such long term stability be maintained in fluids, such as blood, which have a tendency to coagulate on the surface of any foreign body inserted into the fluid.

SUMMARY OF THE INVENTION

The reference electrode of the present invention includes a hollow cylindrical housing member having enclosed ends to thereby form a sealed chamber within the housing member. An aperture extends through one of the walls of the housing member. An electrode element is positioned within the chamber of the housing member and is supported by a retaining member. A conductive lead is connected to the electrode and extends out of the housing member. An electrolytic material, such as gelled Ringer's solution, is disposed within the chamber of the cylindrical housing member, and a membrane formed of hydrogel extends across the aperture in the housing member to thereby provide a liquid junction interface between a fluid to be measured and the electrolytic material within the housing member.

The reference electrode of the present invention is preferably disposed on the distal end of an elongated cylindrical tubing to thereby provide a reference electrode catheter for in vivo measurement of body fluids. The conductive lead which is connected to the electrode element extends through a passageway in the tubing to the proximal end of the tubing for connection to an external measuring instrument. Also, the elongated tubing may be provided with a second passageway which is positioned such that the distal end of the second passageway is disposed in proximity to the outer surface of the hydrogel membrane. With this arrangement, a fluid may be passed through the second passageway in order to provide a flushing action across the outer surface of the hydrogel membrane. This arrangement also makes it possible to locate by fluoroscopy the catheter tip by passing a radiopaque fluid through this passageway.

A preferred embodiment of the reference electrode assembly of the present invention for use in potentiometric electroanalysis in body fluids comprises a hollow cylindrical housing member having closed ends to thereby form a sealed chamber within the housing member, the housing member having an communicating with the chamber; an electrode positioned within the chamber; a conductive lead connected to the electrode and extending out of the housing member; retainer means positioned within the housing member for supporting the electrode; electrolytic material disposed within the chamber of the cylindrical housing member and in contact with the electrode; and a biocompatible porous liquid junction comprised of a hydrogel being positioned across the aperture in the housing member so as to form an ion diffusion control barrier between body fluids to be measured and the electrolytic material within the chamber in the housing member for providing a stable liquid junction potential in body fluids to provide a substantially voltage stable reference electrode. Such assembly can be combined with and mounted at the distal end of a catheter which is connected to the housing member.

BRIEF DESCRIPTION OF THE DRAWINGS

The present invention will become more apparent from the following detailed description, taken in conjunction with the following drawings, wherein:

FIG. 1 is an elevational view, taken partly in cross-section, of an embodiment of the reference electrode of the present invention disposed on the end of a catheter;

FIG. 2 is an enlarged cross-sectional view of the reference electrode and the distal end of the catheter of FIG. 1;

FIG. 3 is a graph illustrating the drift in the electrical potential developed by the reference electrode of the present invention; and, FIG. 4 is a graph illustrating the drift in electrical potential of a prior art reference electrode which utilizes a liquid junction comprised of a polypropylene membrane coated with a surface active agent.

DETAILED DESCRIPTION OF THE DRAWINGS

Referring now to FIG. 1, there is illustrated an in vivo reference electrode catheter 10 which is comprised of a reference electrode assembly 12, disposed on the distal end of an elongated tubing member 14. The tubing member 14 is formed of a flexible material, such as polyvinyl chloride, polyurethane, polyethylene or polypropylene, and is of a small outside diameter such that the tubing may be used for indwelling applications within the human body. The tubing member 14 includes a pair of passageways 16, 18, which extend throughout the entire length of the tubing member 14.

The reference electrode assembly 12 includes a cylindrical housing member 20 having an internal chamber 22 formed therein. Positioned within the chamber 22 is an electrode element 24 which is mounted on and supported by a retainer member 26. The electrode element preferably takes the form of a silver-silver chloride wire, and the retainer member 26 is formed of an insulative material which is molded on to the electrode element 24. The retainer member 26 extends through an end/wall 28 of the housing member 20 and is hermetically sealed in the end/wall 28 by use of an O-ring 30.

The cylindrical housing member 20 also includes an aperture which extends through a side/wall of the housing member 20. A membrane 34 formed of hydrogel is positioned across the aperture 32 and is sealed to the housing member 20 so as to provide a hermetic seal between the edges of the membrane 34 and the housing 20. The chamber 22 is filled with an electrolytic material, such as gelled Ringer's solution, Dulbecco's solution, Hank's solution or saline.

The membrane 34 is constructed of a hydrogel such as a polyhydroxyalkylmethacrylate. The membrane 34 preferably takes the form of polyhydroxyethyemethacrylate (pHEMA) but may also be formed of polyglyceryl methacrylate (pGMA), polyhydroxypropyl methacrylate (pHPMA), polyhydroxyethoxyethyl methacrylate (pHEEMA), polyhydroxydiethoxyethyl methacrylate (pHDEEMA), polymethoxyethyl methacrylate (pMEMA) polymethoxyethoxyethyl methacrylate (pMEEMA), polymethoxydiethoxyethyl methacrylate (pMDEEMA), poly 2,3-dihydroxypropyl methacrylate (pDHPRA) or a combination of these polymers.

Other hydrogels may be used to fabricate the membrane 34 such as poly n-vinyl-2-pyrrolidine (pNVP), polyvinyl alcohol (pVA) polyacrylamide (pAAm) and its derivatives, poly methacrylamide and its derivatives, along with copolymers or other combinations of these polymers.

Suitable monomers to polymerize for hydrogels for the membrane 34 and for example the neutral monomers hydroxyalkyl methacrylate, acrylamide derivatives, n-vinyl pyrrolidone, hydrophobic acrylics; the acidic or anionic monomers acrylic acid derivatives, crotonic acid, sodium styrene sulfonate and the basic or cationic monomers aminoethyl methacrylate derivatives and vinyl pyridine.

With the preferred membrane 34, polyhydroxyethylmethacrylate (pHEMA) was polymerized using ammonium persulfate as initiator tetraethyleneglycoldimethacrylate (TEGDMA) as crosslinking agent, and ethylene glycol as a solvent. HEMA monomer (Sipomer CL-100) was obtained from Alcolac, Inc., Baltimore, Maryland. Ethylene glycol and ammonium persulfate used were reagent grade from J. T. Baker, Inc. TEGDMA was obtained from Tridom Fluka.

These materials were combined to form the prepolymer mixture as follows: a mixture of 75% by volume HEMA monomer, 25% ethylene glycol and 0.15% TEGDMA. This mixture was combined under nitrogen atmospher with ammonium persulfate, 1% by weight in distilled water, in a 6.7 to 1.0 ratio by volume. The prepolymer mixture was then placed, under nitrogen, in polymerization chambers which were pressurized to $10^3$ mm Hg with nitrogen and placed in a 50° C. oven for at least two hours.

Prior to placing the prepolymer in the oven, the material was put into 1 ml plastic syringes which were capped with appropriate T-valves, pressurized, and then placed in the oven.

As is illustrated, the electrode element 24 is coupled through an electrical connector 36 to a conductive lead 38. The conductive lead 38 extends through the passageway 18 in the tubing member 14 from the distal end to the proximal end of the tubing member 14. The conductive lead 38 is connected to an electrical terminal 40 which is adapted to be connected to conventional testing equipment.

The other passageway 16 provides a channel for either the infusion of a calibrating liquid or for the infusion of a liquid which serves to flush the outer surface of the membrane 34 of any impurities which may form on this surface. In addition, a radiopaque fluid may be injected through the passageway 42 to provide an indication of the position of the distal end of the catheter by fluoroscopic methods.

Accordingly, the passageway 16 is positioned such that the distal end 42 of the passageway 16 is disposed in proximity to the outer surface of the membrane 34. With this configuration, it is possible to provide a flushing action or radioapaque dye injection across the outer surface of the membrane 34 by infusion of a liquid through the passageway 16. The other end of the passageway 16 is coupled through a tubing 44 to a fluid connection element 46 which is adapted to be connected to a source of pressurized fluid.

FIGS. 3 and 4 illustrate the improved stability of the reference electrode of the present invention as compared to that of a prior art reference electrode having a liquid junction formed of polypropylene coated with a surface active agent. More particularly, the reference electrode which was used to generate the graph illustrated in FIG. 3 was formed of polyhydroxyethylmethacrylate (pHEMA) which was fabricated as previously discussed. The reference electrode which was utilized to generate the graph as shown in FIG. 4 was constructed with a liquid junction interface formed of polypropylene with a surface active agent. As is apparent from a review of FIGS. 3 and 4 the reference electrode of the present invention provides a high degree of stability over long periods of time, i.e. up to 48 hours. The prior art reference electrode had a high rate of drift, i.e. a drift in potential from approximately 36 to 43 milivolts over a 48-hour period.

It is therefore possible by use of the present invention to obtain a more stable reference electrode potential than has been possible with prior art reference electrodes. It is believed that the improved stability of the present invention is a result of the fact that the hydrogel material is more biocompatible with fluids of the human body, and in particular, with blood. With this improved biocompatability, there is a decrease in the interfacial interactions at the surface of the hydrogel which affect the stability of the liquid junction potential.

In view of the above, it will be appreciated that the reference electrode of the present invention provides far superior results when utilized to measure blood samples than has been possible with prior art reference electrodes.

Although the present invention has been described in detail with regard to a preferred embodiment thereof, it will be apparent to those skilled in the art that various modifications may be made to the described apparatus, without departing from the spirit and scope of the present invention.

What is claimed is:

1. A reference electrode catheter for use in potentiometric electroanalysis in body fluids comprising:
    an elongated cylindrical tubing having proximal and distal ends and having a passageway extending throughout the entire length thereof;
    a hollow cylindrical housing member being mounted at the distal end of said tubing and having enclosed ends to thereby form a sealed chamber within said housing member, an aperture extending through a wall of said housing member and communicating with said chamber;
    an electrode positioned within said chamber;
    a conductive lead connected to said electrode and extending out of the housing member and through said passageway of said tubing to the proximal end of said tubing;
    retainer means positioned within said housing member for supporting said electrode;
    electrolytic material disposed within the chamber of the cylindrical housing member and in contact with said electrode; and,
    a biocompatible porous liquid junction comprised of a hydrogel being positioned across said aperture in said housing member so as to form an ion diffusion control barrier between body fluids and the electrolytic material within the chamber in said housing member for providing a stable liquid junction potential in body fluids to provide a substantially voltage stable reference electrode.

2. A catheter as defined in claim 1 wherein said hydrogen biocompatible porous liquid junction is formed of poly(hydroxethylmethacrylate).

3. A catheter as defined in claim 1 wherein said hydrogel biocompatible porous liquid junction is comprised of a selected one of the group consisting of: poly(hydroxyethylmethacrylate), poly(glyceryl methacrylate), poly(hydroxypropyl methacrylate), poly(hydroxyethoxyethyl methacrylate poly(hydroxydiethoxyethyl methacrylate), poly(methoxyethyl methacrylate), poly(methoxyethoxyethyl methacrylate), poly(methoxydiethoxyethyl methacrylate), poly(2,3-dihydroxypropyl methacrylate).

4. A catheter as defined in claim 1 wherein said elongated cylindrical tubing has a second passageway extending throughout the entire length thereof, the second passageway being positioned such that the distal end of the passageway is disposed in proximity to an outer surface of the hydrogel biocompatible porous liquid junction so that fluid passing through said second passageway in a direction from the proximal end to the distal end of the elongated cylindrical tubing provides a flushing action across the outer surface of the hydrogel biocompatible porous liquid junction.

5. A catheter as defined in claim 4 wherein said electrolytic material is gelled Ringer'solution.

6. A catheter as defined in claim 1 wherein said electrolytic material is gelled Ringer's solution.

7. The catheter of claim 1 wherein said aperture is in a side wall of said housing member.

8. The catheter of claim 1 wherein said electrode is made, at least in part, of silver/silver chloride.

9. A reference electrode assembly for potentiometric electroanalysis in body fluids comprising:
    a hollow cylindrical housing member having enclosed ends to thereby form a sealed chamber within said housing member, an aperture extending through a wall of said housing member and communicating with said chamber;
    an electrode positioned within the chamber;
    a conductive lead connected to the electrode and extending out of the housing member;
    retainer means positioned within said housing membr for supporting said electrode;
    electrolytic material disposed within the chamber of the cylindrical housing member and in contact with said electrode; and
    a biocompatible porous liquid junction comprised of a hydrogel being positioned across said aperture in said housing member so as to form an ion diffusion control barrier between body fluids to be measured and the electrolytic material within the chamber in said housing member for providing a stable liquid junction potential in body fluids to provide a substantially voltage stable reference electrode.

10. A reference electrode assembly as defined in claim 9 wherein said hydrogel biocompatible porous liquid junction is poly(hydroxyethylmethacrylate).

11. A reference electrode assembly as defined in claim 9 wherein said hydrogel biocompatible porous liquid junction is comprised of a selected one of the group consisting of: poly(hydroxyethylmethacrylate), poly(glyceryl methacrylate), poly(hydroxypropyl methacrylate), poly(hydroxyethoxyethyl) methacrylate, poly(hydroxydiethoxyethyl methacrylate), poly(methoxyethyl methacrylate), poly(methoxyethoxyethyl methacrylate), poly(methoxydiethoxyethyl methacrylate), poly(2,3-dihydroxypropyl methacrylate).

12. A reference electrode assembly as defined in claim 9 wherein said electrolytic material is gelled Ringer's solution.

13. A reference electrode assembly as defined in claim 9 wherein said biocompatible porous liquid junction is comprised of hydrogel formed by polymerizing a selected one from the group of monomers comprising: hydroxyalkyl methacrylate, acrylamide derivatives, n-vinyl pyrrolidene, hydrophobic acrylics, acrylic acid derivatives, crotonic acid, sodium styrene sulfonate, aminoethyl methacrylate derivatives and vinyl pyridine.

14. The reference electrode assembly of claim 9 wherein said aperture is in a side wall of said housing member.

15. The reference electrode assembly of claim 9 wherein said electrode is made, at least in part, of silver/silver chloride.

16. A reference electrode assembly as defined in claim 9 combined with a catheter connected to said housing member and comprising a cylindrical tubing having proximal and distal ends and having a passageway extending throughout the entire length thereof and wherein said conductive lead extends through said passageway throughout the length of said lead to said housing member.

17. A reference electrode assembly and catheter combination as defined in claim 16 wherein said cylindrical tubing has a second passageway extending throughout the entire length thereof, the second passageway being positioned such that the distal end of the passageway is disposed in proximity to an outer surface of the hydrogel biocompatible porous liquid junction so that fluid passing through said second passageway in a direction from the proximal end to the distal end of the cylindrical tubing provides a flushing action across the outer surface of the hydrogel biocompatible porous liquid junction.

18. A reference electrode assembly and a catheter combination as defined in claim 17 wherein said electrolytic material is gelled Ringer's solution.

* * * * *

UNITED STATES PATENT OFFICE
CERTIFICATE OF CORRECTION

PATENT NO. : 4,432,366

DATED : Feb. 21, 1984

INVENTOR(S) : Gary S. Margules

It is certified that error appears in the above-identified patent and that said Letters Patent are hereby corrected as shown below:

On the title page:

Under [73] Assignee: Change "CORDIS CORPORATION, Miami, Fla." to --CORDIS EUROPA, N.V., Roden, The Netherlands--

Signed and Sealed this

Eleventh Day of December 1984

[SEAL]

Attest:

Attesting Officer

GERALD J. MOSSINGHOFF

Commissioner of Patents and Trademarks